(12) United States Patent
James et al.

(10) Patent No.: US 8,329,894 B2
(45) Date of Patent: Dec. 11, 2012

(54) PROCESS FOR THE PRODUCTION OF ESTERS OF SUGARS AND SUGAR DERIVATIVES

(75) Inventors: Kenneth James, Reading (GB); James Frederick Smith, Reading (GB)

(73) Assignee: Sebus Limited, Reading (GB)

( * ) Notice: Subject to any disclaimer, the term of this patent is extended or adjusted under 35 U.S.C. 154(b) by 426 days.

(21) Appl. No.: 12/298,457

(22) PCT Filed: Apr. 26, 2007

(86) PCT No.: PCT/GB2007/001529
§ 371 (c)(1),
(2), (4) Date: Dec. 12, 2008

(87) PCT Pub. No.: WO2007/125328
PCT Pub. Date: Nov. 8, 2007

(65) Prior Publication Data
US 2009/0259033 A1    Oct. 15, 2009

(30) Foreign Application Priority Data
Apr. 28, 2006   (GB) .................................. 0608512.0

(51) Int. Cl.
*C07H 13/06* (2006.01)
*C07C 67/03* (2006.01)
(52) U.S. Cl. ..................................................... 536/119
(58) Field of Classification Search ................... 536/119
See application file for complete search history.

(56) References Cited

U.S. PATENT DOCUMENTS

| | | | |
|---|---|---|---|
| 3,349,081 A | 10/1967 | Nobile | |
| 3,714,144 A | 1/1973 | Feuge et al. | |
| 3,963,699 A | 6/1976 | Rizzi et al. | |
| 3,996,206 A | 12/1976 | Parker et al. | |
| 4,298,730 A * | 11/1981 | Galleymore et al. | 536/119 |
| 4,377,685 A | 3/1983 | Bouniot et al. | |
| 4,518,772 A | 5/1985 | Volpenhein | |
| 5,490,995 A * | 2/1996 | Corrigan | 426/531 |
| 5,491,226 A * | 2/1996 | Kenneally | 536/115 |
| 5,837,669 A | 11/1998 | Petit et al. | |
| 2008/0071079 A1 | 3/2008 | James et al. | |

FOREIGN PATENT DOCUMENTS

| | | |
|---|---|---|
| DE | 1193026 | 5/1965 |
| DE | 4131505 | 3/1993 |
| EP | 0404226 | 6/1990 |
| EP | 0798308 | 3/1997 |
| GB | 1499989 | 2/1978 |
| GB | 2081266 | 2/1982 |
| GB | 2361918 | 7/2001 |
| WO | 90/03840 | 4/1990 |
| WO | 93/06114 | 4/1993 |
| WO | 03/090669 | 11/2003 |

OTHER PUBLICATIONS

Feuge et al, J. Am. Oil Chemists' Soc. 1970, 47, 56-60.*
Feuge et al., "Preparation of Sucrose Esters by Interesterification," J. Am. Oil Chemists Soc., 1970, 56-60, vol. 47, No. 2.
Rizzi et al., "A Solvent-free Synthesis of Sucrose Polyesters," J. Am. Oil Chemists Soc., 1978, 398-401, vol. 55.
Louis Bobichon, "A Sugar Ester Process and Its Application in Calf Feeding and Human Food Additives," ACS Symposium Series 41, 1977, 115-120.

* cited by examiner

*Primary Examiner* — Shaojia Anna Jiang
*Assistant Examiner* — Ganapathy Krishnan
(74) *Attorney, Agent, or Firm* — Beresford & Co

(57) ABSTRACT

A process for the production of an ester of a non-reducing sugar or sugar derivative comprises reacting the non-reducing sugar or sugar derivative with a triglyceride of a fatty acid or a fatty acid ester of a monohydric alcohol in air, substantially in the absence of a solvent and under heterogeneous reaction conditions in which the sucrose and alkyl ester or triglyceride are present as separate phases, at a temperature in the range of from 110° C. to 140° C., wherein the reaction is conducted in the presence of a potassium soap but in the absence of an alkaline component. The process enables esters of sugars and sugar derivatives to be produced at lower temperatures than hitherto and in a much simpler process.

26 Claims, 1 Drawing Sheet

PROCESS FOR THE PRODUCTION OF ESTERS OF SUGARS AND SUGAR DERIVATIVES

This invention relates to the production of esters of non-reducing sugars or sugar derivatives, and especially, although not exclusively, to sucrose esters.

Esters of sucrose with fatty acids, particularly the sucrose mono-esters and di-esters, are potentially very important materials, and have a number of extremely useful properties. For example, sucrose esters as defined under E473 are non-toxic, odourless, non-irritating to the skin, and when ingested, they hydrolyse to form normal food products. They may, for example, be employed as surfactants, and, unlike most other surfactants are biodegradable under both aerobic and anaerobic conditions. They are very good emulsifiers, and perform well as detergents, either alone or in combination with anionic surfactants, and may be formulated as either high foaming or low foaming detergents. Accordingly, they may be used generally as domestic or industrial detergents, and also in specialized uses such as additives for foodstuffs, for example for treating fresh fruit and vegetables, animal feeds, cosmetics, pharmaceuticals and agricultural chemicals. They may be employed as lubricants, plasticizers (with or without glycerides), emollients, and as emulsifiers. In addition to sucrose esters, sucroglycerides are of considerable commercial importance. Sucroglycerides are commonly mixtures of sucrose esters and glycerides as defined under E474.

However, in spite of possessing such advantages, sucrose esters have never been exploited to their full potential, because of difficulties arising from their production. Many processes have been proposed for their manufacture but because of technical and economic disadvantages, it is still difficult to achieve large-scale industrial production at low cost.

Sucrose esters cannot be prepared by the direct esterification of sucrose with a fatty acid, but may be prepared by transesterification with a fatty acid ester. Most of the known transesterification processes are carried out in a solvent, for example dimethylformamide (DMF) or dimethylsulphoxide (DMSO), and are performed at an elevated temperature in the region of 90° C. in the presence of an alkaline catalyst, for example potassium carbonate, using the methyl ester of the fatty acid.

In the transesterification process, it is necessary to remove water in order to drive the reaction equilibrium in the right direction since the presence of water will cause the reaction to reverse. The water may be removed by heating the system above 100° C. and/or by reduced pressure. In addition, it may be necessary to employ a dry nitrogen blanket in order to prevent traces of water in the air from contaminating the reaction mixture. In the transesterification process it is also preferable to prevent or minimise the ingress of oxygen in order to prevent or minimise oxidation of any unsaturated reactants. The need for anhydrous conditions, the prolonged heating sometimes under reduced pressure, the use of a nitrogen blanket to prevent contamination by water or oxygen and the use of a solvent are serious disadvantages both in terms of the economics of the process, but also because all traces of the solvent must be removed from the product.

Furthermore, the solvent will remain in the reaction product, and such solvent-based processes require the subsequent removal of the solvent if the products are to be employed in foodstuffs. The relatively limited solubility of sucrose in organic solvents also requires a large excess of solvent to be employed, all of which must be removed from the final product and recovered.

It has been proposed to conduct the transesterification reaction without the presence of a solvent, but such processes generally suffer from a number of disadvantages, for example, relatively long reaction times in the order of 8 to 16 hours, relatively low yields, for example in the order of 15 to 20%, or relatively complex and expensive apparatus employing nitrogen or carbon dioxide blankets or conducting the process in a vacuum.

A number of patent documents disclose the use of microwaves for the transesterification reaction, for example EP-A-0 798 308 (CECA S. A.) which describes reacting dianhydro-1,4:3,6-D-glucitol with methyl dodecanoate in a dimethylformamide solvent under the action of microwaves.

WO 03/090669 (Aldivia S. A.) describes a method for the production of esterified polyhydroxylated alcohols, for example sorbitol, mannitol or xylitol, by esterification, transesterification or interesterification using microwaves in an atmosphere deprived of oxygen.

GB-A-2,361,918 (Interpole Ltd.) describes a process for the transesterification of sucrose using a NaOH catalyst under vacuum and employing microwaves, which purports to generate the octaester.

A number of other references document the transesterification of sugars at elevated temperatures without microwave heating and in the absence of a solvent. For example, R. Feuge et al (J. Am. Oil Chemists Soc. Vol 47 No. 2 56-60 (1970) and U.S. Pat. No. 3,714,144 propose the production of sucrose esters from by reacting molten sucrose with alkyl esters at temperatures of about 185° C. in the presence of an alkali metal soap, and under homogeneous conditions. The alkali metal soaps were specially prepared in order to ensure that no traces of alkali were present which were found to cause rapid darkening and degradation of the sucrose. In order to solubilise the ester in the sucrose, esters containing hydroxyl groups were used, for example partial esters of glycerol, methyl carbitol or methyl cellosolve.

Rizzi et al (J. American Oil Chemists' Soc. Vol. 55 398 (1978) proposes two processes for the production of sucrose esters by the reaction of sucrose with methyl esters under homogeneous conditions. In one reaction catalysed by an alkali metal soap, the reaction was performed at temperatures of at least 165° C. under vacuum and was performed in two stages to maintain a homogeneous mixture, while in another reaction, also described in U.S. Pat. No. 3,963,699, also conducted under vacuum, very strong alkalis such as alkali metals, alkali metal hydrides or alkali metal alkoxides were employed to form the sucrate anion.

U.S. Pat. No. 4,298,730 (Galleymore et al) describes a transesterification process for producing sucrose esters employing a potassium soap under alkaline conditions. The sucrose is reacted with esters having sufficient mono- and diglycerides having high hydroxyl values, presumably for the reason given in the Feuge et al. paper.

U.S. Pat. No. 4,518,772 (Volpenhein) describes a transesterification reaction of sucrose with fatty acid esters conducted in a homogeneous melt and under alkaline conditions.

U.S. Pat. No. 5,491,226 (Kenneally) describes a process for forming sucrose esters that is conducted using a potassium stearate soap and an effective amount of a basic catalyst. The process is a two-stage process of the type described in the Rizzi et al paper, in which additional methyl ester is added in the second stage, and is conducted under vacuum.

U.S. Pat. No. 5,490,995 (Corrigan) also describes a two-stage process for producing sucrose esters in which additional alkyl ester is added to the reaction mix in the second stage, and which is conducted under vacuum employing potassium stearate.

The present invention provides a process for the production of an ester of a non-reducing sugar or sugar derivative, which comprises reacting the sugar or sugar derivative with a fatty acid alkyl ester at an elevated temperature, wherein the reaction is conducted in the presence of a potassium soap but in the absence of an alkaline component.

In particular, according to the invention, there is provided a process for the production of an ester of a non-reducing sugar or sugar derivative, which comprises reacting the non-reducing sugar or sugar derivative with a triglyceride of a fatty acid or a fatty acid ester of a monohydric alcohol in air, substantially in the absence of a solvent and under heterogeneous reaction conditions in which the sucrose and alkyl ester or triglyceride are present as separate phases, at a temperature in the range of from 110° C. to 140° C., wherein the reaction is conducted in the presence of a potassium soap but in the absence of an alkaline component.

By employing the processing conditions and reactants according to the invention, it is possible to obtain acceptable quantities of sugar esters by a very simple process. In particular, we have found that conducting the reaction with a heterogeneous reaction mixture obviates the need for special precautions required for forming a homogeneous mixture, which was always considered necessary for intimate mixing of the reactants, such as the use of specific hydroxyl group-containing reactants such as mono- or diglycerides as the alkyl esters, or two-stage processes in which part of the alkyl ester is added in a first stage and the remainder of the alkyl ester is added only after a homogeneous reaction mixture of mono esters has been formed. In addition, the use of a heterogeneous reaction mixture removes the need for high temperatures (e.g. about 160-185° C.) which can cause degradation of the sugar especially in the presence of alkalis, even trace amounts of alkali in the soaps. Lower reaction temperatures had been thought to reduce the effectiveness of soaps as interesterification catalysts and to promote disproportionation of the sucrose esters (see Feuge et al) and indeed Rizzi et al reported that partial esters of sucrose disproportionated, catalysed by lithium oleate, with the loss of sucrose due to caramelization. Furthermore, we have found that alkaline catalysts, which are generally regarded in the art as being required for all transesterification reactions, are not, in fact, necessary for acceptable yields provided that a potassium soap is present. The absence of any strong alkalis such as sodium hydroxide, potassium carbonate or sodium methoxide as have been employed in the prior art has the advantage that the soap will not undergo any reaction with the ester or triglyceride, so that any soap occurring in the product will be well defined, and will reduce the tendency of the sugar esters to disproportionate or the tendency of the sugar to decompose.

The term "alkaline component" is intended to mean a component formed from a conjugate acid/base having a pKa value greater than 9. pKa values are useful for describing the strength of acids and alkalis in nonaqueous solvents or anhydrous conditions, and may be found for conjugate acids/bases in a number of publications, for example Hendrickson, Cram and Hammond, *Organic Chemistry* 3$^{rd}$ Edition, McGraw-Hill or by Hans Reich (http://www.chem.wisc.edu/areas/reich/pkatable/). Typically a base having a pKa value not more than 9 will correspond to one that is weaker than ammonia (the conjugate acid being $NH_4^+$). Preferably any such component will have a pKa of not more than about 6 to 6.5 corresponding to that of the bicarbonate ($HCO_3^-$) ion. According to this aspect of the invention, highly alkaline components such as alkali metal hydroxides or carbonates are not present, and are not necessary, since we have found that the transesterification reaction proceeds in the presence of the potassium soap rather than by the presence of any alkaline catalyst. Thus, although the reaction will be conducted in anhydrous conditions, if water were added to the reaction mixture, the resulting mixture would generally have a pH given by the potassium soap. The absence of any strong alkalis such as sodium hydroxide, potassium carbonate or sodium methoxide as has been employed in the prior art has the advantage that the soap will not undergo any reaction with the ester or triglyceride so that any soap occurring in the product will be well defined as explained below. However, unlike the reactions described in the Fuege et al paper above, and in U.S. Pat. No. 3,714,144, it is not necessary for any special preparation of the potassium soap to be employed, and that commercially available soaps may be used. It is preferred, although not necessarily essential, that the reaction is conducted substantially in the absence of any components having a pKa lower than 4. This is because carboxylic acids generally have a pKa in the region of 4 to 5, so that it is possible that substantial quantities of conjugate acids with a pKa less than about 4 may react with the potassium soap to produce free fatty acid and the potassium salt of the conjugate acid.

The reactants may be heated by any appropriate method, for example by employing microwaves as mentioned above, or by employing means other than microwaves such as by thermal conduction from a reaction vessel. The vessel may be a jacketed vessel in which case any appropriate heating medium may be employed, for example superheated steam, oil or other material, or heat may be provided in other ways, for example by employing a heating element that is heated by electrical resistance heating or by induction heating.

Thus, according to another aspect, the invention provides a process for the production of an ester of a non-reducing sugar or sugar derivative, which comprises reacting the sugar or sugar derivative with a fatty acid alkyl ester at an elevated temperature, wherein the reaction is conducted in the presence of a potassium soap and the reactants are heated by means other than microwave radiation, for example by means of thermal conduction.

The process according to the invention may employ means other than microwaves to heat the reactants in addition to the absence of alkaline components.

The term "non-reducing sugar derivative" is intended to mean that sugar derivative, rather than the sugar from which it is formed, is not oxidized by reagents such as Fehling's solution etc. Thus, the sugar derivative may be formed from a reducing sugar provided that any aldehyde or keto group in the sugar has been protected or removed in forming the derivative.

The process may be employed to produce esters of any of a number of non-reducing sugars or sugar derivatives. Advantageously the non-reducing sugar or sugar derivative comprises a non-reducing disaccharide, a glycoside of a mono- or disaccharide, or a polyol that has been formed by reduction of a mono- or disaccharide. Thus, sucrose or trehalose may be used, especially sucrose. Preferred sugars for forming the glycosides include ketoses such as fructose, sorbose, tagetose, psicose; pentoses such as lyxose, ribose, arabinose or xylose; aldoses such as allose, altrose, glucose, mannose, gulose, idose, galactose or talose; or $C_4$ sugars such as erythrose or threose. The glycosides may be formed from straight-chain or branched lower ($C_1$ to $C_6$) alkanols, preferably methanol, ethanol or propanol.

Any of the reducing sugars may be employed to form a polyol, sorbitol, mannitol and lactitol being preferred.

We have determined, as described in more detail below, that although GB-A-2,361,918 purports to generate sucrose octaester by transesterification with methyl palmitate, no such ester is formed under the reaction conditions described therein or even when longer times, higher temperatures or more catalyst is used. What is important to the formation of esters is the fact that the reaction is conducted in the presence of a potassium soap.

Also, it appears that while at high temperatures, for example in the region of the melting point of sucrose (185° C.), a number of alkali metal soaps may be employed in the reaction with sodium and potassium soaps exhibiting similar performance, and lithium oleate exhibiting the greatest performance (Fuege et al), if the reaction temperature is reduced to that according to the present invention, we have determined that the presence of a potassium soap is necessary for the reaction to proceed, and especially an unsaturated potassium soap, and that soaps of other metals do not enable production of the esters.

The reason why the presence of the potassium soap is important to the reaction is not understood. The soap is a source of readily available potassium ions as well as acting as an emulsifier, which will increase the availability of the sugar or sugar derivative in the ester of the fatty acid, but the ability of the soap to act as an emulsifier does not explain the dramatic effect of the presence of the soap to the reaction or why this effect is specific to potassium.

Without being bound by any particular theory, it is conjectured that the reaction proceeds by the formation of a six coordinate complex between the potassium atom and the hydroxyl groups of the sucrose, leaving two hydroxyl groups free, and that once the complex has been formed, the transesterification involves the reaction of singlet oxygen ($^1O_2$) with the alkyl ester. If this is the case, not only is it not necessary to exclude atmospheric oxygen during the reaction, it is indeed preferred for the reaction to be conducted in the presence of air.

The soap will typically be formed from a fatty acid having a straight-chain or branched, saturated, mono-unsaturated or poly-unsaturated alkyl group having at least 6, preferably at least 12 carbon atoms, but normally not more than 22 and especially not more than 18 carbon atoms. The preferred potassium soaps include potassium oleate, stearate, palmitate, laurate and linoleate, although soaps employing shorter chain fatty acid such as capric or caprylic acid may be used. The potassium soap is preferably included at the commencement of the process rather than being allowed to be formed in situ. It is believed that the very long reaction times required in the prior art solvent-free processes has not been due to the time taken to conduct the transesterification reaction, but rather to the time taken to generate the potassium soap that catalyses the reaction. The process will normally be conducted for a period of up to 5 hours, and may in many cases be conducted for shorter periods, for example up to 2 hours, although in other cases, especially where esters of sugars with multiple fatty acid groups are prepared, it may be necessary to conduct the process for longer periods, for example for up to 15 hours.

The use of the potassium soap as a starting material has the further advantage over forming soaps by reaction of alkyl esters with an alkali in that the fatty acid component of the soap will be well defined rather than being a mixture of unknown or incompletely known composition. Because the soap does not appear to take part in the transesterification reaction, the same soap will be present in the reaction products, which enables extraction to be optimised. Alternatively, if the sugar ester is intended to be used as a detergent, the soap can be retained in the product and will have defined solubility properties. In addition, it is possible for the soap to have a different fatty acid from that employed in the transesterification reaction. For example, if it is desired to form sucrose stearate, it is not necessary to employ potassium stearate as the catalyst, but instead potassium oleate, which gives a relatively fast reaction, may be used.

Preferably, although not necessarily, the reaction will be conducted substantially in the absence of a solvent and in air. It is possible to include some solvent in the reaction mix, although there will be no advantage to this and the presence of a solvent will have the disadvantage that the solvent will need to be removed. Similarly, it is possible to employ an inert gas blanket or a vacuum, but this also is not necessary and some of the advantage of the invention will thus be lost in terms of a simplified process.

By the phrase "in air" is meant that the process is conducted in the atmosphere without any inert gas being provided or without the reaction being conducted under a vacuum, in order to prevent atmospheric moisture or oxygen reaching the reactants. It is not necessary for the reaction to be conducted at atmospheric pressure: super- or sub-atmospheric pressures may be employed if desired, but no special techniques or precautions are required. Typically the process will be conducted at pressures above 500 mbar.

The process according to the invention has the advantage that it is possible to conduct the reaction to produce a relatively high yield in a relatively short period of time, for example in less than 5 hours, typically from 1 to 5 hours. The reduction in length of time for the reaction enables the reaction to be conducted in the presence of air without atmospheric oxygen causing excessive degradation of the unsaturated components of the reaction mix and so the reaction may be performed without the need to provide a vacuum or an inert gas blanket.

The process according to the invention is conducted at an elevated temperature, but this should not be so high as to initiate degradation of the reactants and consequential colour formation. Thus, as will be appreciated, the process will normally employ heterogeneous reaction conditions in which the sucrose and the alkyl ester reactants are present as separate phases. The process will normally be conducted at a temperature in the range of from 110° C. to 140° C. and especially from 120° C. to 135° C.

The fatty acid alkyl ester may have a straight-chain or branched fatty acid alkyl group which may be mono- or poly unsaturated, and preferably have a length of at least 6, and especially at least 12 carbon atoms, but usually no more than 22 and preferably no more than 18 carbon atoms. The alkyl ester may be formed from a fatty acid and a monohydric alcohol or a polyol, preferably an alcohol having a lower alkyl group, for example having up to six carbon atoms, and especially methanol, ethanol or glycerol.

The proportion of sugar or sugar derivative to ester will depend on the desired composition of the product. Normally the reaction mix will contain at least 0.1 mole of the non-reducing sugar or sugar derivative, per mole of alkyl ester, but usually not more than 2 moles of sugar or sugar derivative per mole of alkyl ester. It is preferred for the quantity of ester that is used to be such that there is at least one mole of fatty acid units of the ester per mole of sugar or sugar derivative, and especially a stoichiometric excess of fatty acid units. For example, to form a sugar diester, a molar ratio of 1:2 for sugar:methyl ester is employed, and a molar ratio of 3:2 for sugar:triglyceride is used.

Preferably at least 0.4 mole of potassium soap is used per mole of sugar since quantities significantly below this are generally ineffective and the reaction is incomplete. The preferred quantity of potassium soap is from 1 to 2 moles per mole of sugar or sugar derivative. At the upper limit, the viscosity of the reaction medium increases significantly, although it may be possible to use more soap, for example up to 3 moles per mole of sugar or sugar derivative, and especially up to 2.5 moles per mole of sugar or sugar derivative if the viscosity of the medium does not render this impractical.

If microwave radiation is employed, it may have any of a number of frequencies, although it has been found that radiation of 2.45 GHz frequency normally employed in domestic microwave apparatus is effective for promoting the reaction. The radiation may be pulsed or continuous, and will preferably be employed in a range of from 120 to 2000 W per kg of reaction mix. Similar power inputs will advantageously be employed for other methods of heating for example by thermal conduction.

The crude reaction product will normally contain a mixture of esters of the non-reducing sugar or sugar derivatives, unreacted sugar or derivative, unreacted alkyl fatty acid esters and soaps. For most applications the esters of the sugar or sugar derivative will need to be extracted from the reaction mixture. A solvent extraction method is preferably employed in which different solvents in which the various reaction products are soluble are used. For example, a solvent in which sucrose is insoluble, such as a lower (e.g. $C_1$-$C_6$) alkanol, may be used to separate the sucrose esters and alkyl esters from unreacted sucrose, followed by a further solvent extraction step using a solvent in which either the alkyl ester or the sucrose ester component is soluble in order to separate the two.

In one preferred process, the reaction mix is treated with sec-butanol to separate sucrose from the other materials. The extraction may be employed at room temperature while stirring, and employing from 2 to 10 parts of solvent, preferably from 3 to 5 parts of solvent, and especially about four parts of solvent per part of reaction mix. Insoluble material, mainly sucrose, may be removed by filtration or, more preferably, by centrifugation, and may be reused. If desired, an ion exchange resin may be employed, to convert any soaps to free fatty acids in which case it is convenient to add the ion exchange resin at this stage. This enables the free fatty acids to be extracted with the unreacted methyl esters.

The liquid phase will contain, apart from the solvent, the sucrose esters and the alkyl ester reactant employed for the transesterification. After removal of the solvent, for example by evaporation, the sucrose esters and the alkyl ester may be separated by a further solvent extraction step, for example using a solvent such as ethyl acetate in which the alkyl ester and free fatty acids if present are soluble. Typically from 2 to 10 parts of solvent, preferably from 3 to 5 parts of solvent, and especially about 4 parts of solvent will be employed per part of the solid phase. In addition, it is preferred for the solvent to be cold, for example at a temperature of not more than 5° C., and preferably at about −5° C. In this case, the solid phase will contain substantially only the sucrose esters which may be employed if desired without further processing other than drying if necessary.

The solvent may be removed from the liquid phase for example by evaporation, and both the solvent and the alkyl ester may be recycled.

The following Examples illustrate the invention. Reference is made in Examples 25 and 26 to FIGS. 1 and 2:

Methyl palmitate and cocoate were prepared from commercially available palm or coconut oil by reaction with methyl alcohol using either p-toluene sulphonic acid or Sodium Methoxide As The Catalyst.

CREATION OF CRUDE SUCROSE ESTER REACTION PRODUCT

EXAMPLE 1

158 grams (approximately 0.55 moles) of Methyl palmitate from naturally occurring palm oil (with an assumed formula $CH_3(CH_2)_{14}COOCH_3$) was mixed with 41.6 grams of analytical grade potassium oleate (approximately 0.13 moles) and 90 grams of comminuted sugar (approximately 0.26 moles) and mixed thoroughly. The reaction mass was then heated in an oil bath until the temperature reached 125° C. Heating was continued for 4 hours maintaining the temperature between 125° C. and 135° C., while stirring the reaction mix continuously. Samples were taken and were analysed by T.L.C. analysis visualizing the reaction products with concentrated sulphuric acid in ethyl alcohol and heating at 110° C. Ester formation was observed after 1, 2, 3 and 4 hours. The reaction was stopped yielding a soft light brown waxy material.

EXAMPLE 1B

Example 1 was repeated with the exception that the quantity of potassium oleate was increased from 41.6 grams (approx. 0.13 moles) to 83.2 grams (approx. 0.26 moles) with the quantities of the other components remaining roughly the same, so that the molar ratios of methyl ester:sucrose:potassium oleate were approximately 2:1:1. After 4 to 5 hours the total quantity of sucrose ester was found to be in excess of 40% by weight as analysed by G.C.

Extraction of Crude Reaction Product

EXAMPLE 2

40 grams of the reaction mass from Example 1 was stirred with 160 grams of sec-butyl alcohol at room temperature for 10 minutes, and the resulting slurry filtered. The residue was dried to a sticky powder consisting of sucrose and some soaps. The filtrate was evaporated to dryness to yield a mixture of sucrose esters, methyl esters and soaps. This was extracted with cold ethyl acetate (125 grams at −5° C.), filtered, and evaporated to dryness, yielding a mobile, light coloured oil consisting of methyl esters. The residue was dried to yield sucrose esters and some soaps.

EXAMPLE 3

40 grams of the reaction mass from Example 1 was extracted with 160 grams of cold ethyl acetate (5° C.) and filtered. The filtrate was evaporated to dryness to yield methyl esters. The residue of sucrose esters, sucrose and soaps was dried, extracted with 120 grams of sec-butyl alcohol, and filtered. The residue was dried to yield sucrose and some soaps. The filtrate was evaporated to dryness to yield sucrose esters.

Determination of Reactant Necessary for Ester Formation

EXAMPLE 4

Example 1 was repeated with the exception that no potassium oleate was present. The reaction was continued for 3 hours at 125-130° C. and samples were taken and analysed by T.L.C. No sucrose ester formation was observed.

EXAMPLE 5

Example 4 was repeated with the exception that pure (96%) methyl palmitate in place of natural methyl palmitate. The reaction was continued for 4 hours at 125-130° C. and samples were taken and analysed by T.L.C. No sucrose ester formation was observed.

EXAMPLE 6

Example 1 using pure (96%) methyl palmitate was repeated with the exception that the potassium oleate was replaced with methyl oleate. The reaction was continued for 4 hours at 125-130° C. and samples were taken and analysed by T.L.C. No sucrose ester formation was observed.

EXAMPLE 7

Example 1 was repeated with the exception that the methyl palmitate was replaced with technical (60%) methyl oleate and that no potassium oleate was present. The reaction was continued for 4 hours at 125-130° C. and samples were taken and analysed by T.L.C. No sucrose ester formation was observed.

In each of Examples 4 to 7, the sucrose tended to form a hard mass. It was concluded that a metal soap was necessary for sucrose ester formation rather than sucrose ester formation being caused by the fatty acid anion or by any other components in the natural esters.

Determination of Scope of the Metal Soap

EXAMPLES 8 to 22

Example 1 was repeated employing a range of metal soaps in the reaction mixture. 0.26 moles of sucrose and 0.55 moles of methyl esters were employed in each case. 0.13 moles of soaps of group I metals, 0.065 moles of soaps of group II metals, and 0.044 moles of soaps of group III metals were employed in order to give the same concentration of soap anion, and the temperature was maintained at a range of 120 to 140° C. Ester formation was determined by T.L.C. as described in Example 1. The results are shown in Table 1

TABLE 1

| Example | Soap | Ester | Sucrose ester formation |
|---|---|---|---|
| 8 | K acetate | Me oleate | No |
| 9 | K acetate + Na oleate | Me oleate | No |
| 10 | K citrate + Na oleate | Me oleate | No |
| 11 | Na oleate | Me oleate | No |
| 12 | Na oleate | Me palmitate | No |
| 13 | Na oleate | Palm oil[1] | No |
| 14 | Na oleate | HPKO[2] | No |
| 15 | K stearate | Me oleate | Yes |
| 16 | K stearate | Me stearate | Yes |
| 17 | Na stearate | Me oleate | No |
| 18 | Ca stearate | Me oleate | No |
| 19 | Ca oleate | Me oleate | No |
| 20 | Li stearate | Me oleate | No |
| 21 | Li oleate | Me oleate | No |
| 22 | Al distearate | Me oleate | No |

[1]triglyceride of $C_{16}$-$C_{18}$ fatty acids
[2]Hydrogenated palm kernel oil (c. $C_{12}$)

It can be seen from the table that soaps of metals other than potassium do not lead to sucrose ester formation, nor do potassium salts of short-chain carboxylic acids such as acetic acid or citric acid, even when sodium oleate is added as an emulsifying agent. Processes in which potassium oleate is employed appear to lead to sucrose ester formation more rapidly than when potassium stearate is used, and it is conjectured that this may be because of the increased solubility of potassium oleate in the reaction medium.

Range and Proportions of Reactants

EXAMPLE 23

Sucrose (approx. 0.13 moles) was reacted with methyl oleate (approx. 0.26 moles) in the presence of potassium oleate (approx. 0.05 moles) while stirring and maintaining the temperature at approximately 125° C. By TLC sucrose esters were found to be present at 1 hour. By GC sucrose mono- and diesters were found to comprise 2.7% of the reaction mix at 5 hours.

EXAMPLE 24

Example 23 was repeated using 0.10 moles of potassium oleate. By TLC sucrose esters were found to be present at 1 hour. By GC sucrose mono- and diesters were found to comprise 34.9% of the reaction mix at 5 hours.

EXAMPLE 25

Example 23 was repeated using 0.15 moles of potassium oleate. By TLC sucrose esters were found to be present at 1 hour. By GC sucrose mono- and diesters were found to comprise 35.9% of the reaction mix at 4 hrs, and 40% at 5 hours. The concentration of sucrose esters is shown in FIG. 1.

EXAMPLE 26

Example 23 was repeated using 0.20 moles of potassium oleate. By TLC sucrose esters were found to be present at 1 hour. By GC sucrose mono- and diesters were found to comprise 36.9% of the reaction mix at 4 hrs, and 39.9% of the reaction mix at 5 hours. The concentration of sucrose esters is shown in FIG. 2.

EXAMPLE 27

Example 25 was repeated using 0.26 moles of methyl stearate in place of methyl oleate. By TLC sucrose esters were found to be present at 1 hour.

EXAMPLE 28

Example 27 was repeated using 0.20 moles of potassium oleate. By TLC sucrose esters were found to be present at 1 hour.

EXAMPLE 29

Example 25 was repeated using 0.15 moles of potassium stearate in place of potassium oleate. By TLC sucrose esters were found to be present at 2 hours.

EXAMPLE 30

Example 29 was repeated using 0.20 moles of potassium stearate. By TLC sucrose esters were found to be present at 2 hours.

EXAMPLE 31

Example 27 was repeated using 0.15 moles of potassium stearate in place of potassium oleate. By TLC sucrose esters were found to be present at 5 hours.

EXAMPLE 32

Example 31 was repeated using 0.20 moles of potassium stearate. By TLC sucrose esters were found to be present at 5 hours.

EXAMPLE 33

Example 25 was repeated using 0.15 moles of potassium linoleate in place of potassium oleate. By TLC sucrose esters were found to be present at 1 hour.

EXAMPLE 34

Example 33 was repeated using 0.2 moles of potassium linoleate. By TLC sucrose esters were found to be present at 1 hour.

EXAMPLE 35

Example 23 was repeated using 0.25 moles of potassium oleate. By TLC sucrose esters were found to be present at 1 hour.

EXAMPLE 36

Example 26 was repeated using 0.087 moles of palm oil in place of methyl oleate. By TLC sucrose esters were found to be present at 3 hours.

EXAMPLE 37

Example 36 was repeated using 0.087 moles of hydrogenated palm kernel oil in place of palm oil. By TLC sucrose esters were found to be present at 2 hours.

EXAMPLE 38

Example 37 was repeated using 0.087 moles of C8/C10 triglyceride in place of hydrogenated palm kernel oil, and potassium caprate in place of potassium oleate. By TLC sucrose esters were found to be present at 2 hours.

EXAMPLE 39

Example 38 was repeated using potassium caprylate in place of potassium caprate. By TLC sucrose esters were found to be present at 1 hour.

EXAMPLE 40

Example 38 was repeated using 0.26 moles of C8/C10 methyl esters in place of C8/C10 triglyceride. By TLC sucrose esters were found to be present at 1 hour.

EXAMPLE 41

Example 40 was repeated using potassium caprylate in place of potassium caprate. By TLC sucrose esters were found to be present at 1 hour.

EXAMPLE 42

Example 36 was repeated using hydrogenated palm kernel oil triglyceride in place of palm oil and potassium laurate ($C_{11}H_{23}COOK$) in place of potassium oleate. By TLC sucrose esters were found to be present at 2 hours.

EXAMPLE 43

Example 42 was repeated using coconut oil in place of hydrogenated palm kernel oil (HPKO) triglyceride. Sucrose esters were found to be present at 2 hours.

EXAMPLE 44

Example 42 was repeated using hydrogenated palm kernel oil methyl esters in place of hydrogenated palm kernel oil triglyceride. By T.L.C., sucrose esters were found at 1 hour.

EXAMPLE 45

Example 43 was repeated using coconut oil methyl esters in place of hydrogenated palm kernel oil triglyceride, and by T.L.C., sucrose esters were found to be present after 1 hour.

From the above Examples, it can be seen that sucrose ester formation is observed for all reactions involving potassium soaps having at least 8 carbon atoms. Ester formation appears to occur somewhat faster when potassium oleate is employed as the catalyst as compared with potassium stearate, and that although ester formation is observed at all potassium soap concentrations, ester formation is considerably increased for soap concentrations above 0.4 moles per mole of sugar or sugar derivative. The Examples were conducted by heating the reaction mixture in an oil bath. Some of the Examples were repeated by employing a domestic microwave oven, without any significant difference in the results.

Some of the above reactions were repeated at the same molar ratio and in the presence of 130 grams of tapioca pearls to provide the substrate for a template reaction, and sucrose esters were obtained. (Glycochemistry, Ed. By P. G. Wang and C. R. Bertozzi, Marcel Dekker Inc (2001) Chapter 1 pp. 1-32).

Formation of Esters of Sugar Derivatives

EXAMPLES 46 to 50

Example 1 was repeated employing lactitol, sorbitol and methyl glucoside in place of sucrose. The methyl ester employed was methyl oleate or methyl stearate. In Examples 46 to 49, 0.26 moles of the sugar derivative, 0.55 moles of the methyl ester, and 0.13 moles of the potassium soap were employed, while in Example 50, 0.26 moles of the methyl ester, 0.13 moles of the sugar derivative and 0.15 moles of the potassium soap were employed. The temperature was maintained at a range of 120° C. to 140° C., and ester formation was determined by T.L.C. as described in Example 1. The results are shown in Table 2, from which it can be seen that ester formation of the sugar derivative was observed in all cases.

TABLE 2

| Example | Soap | Sugar Derivative | Methyl Ester | Ester formed |
|---------|------|------------------|--------------|--------------|
| 46 | K oleate | sorbitol | Me oleate | yes |
| 47 | K oleate | lactitol | Me oleate | yes |
| 48 | K oleate | Me glucoside | Me oleate | yes |
| 49 | K stearate | lactitol | Me stearate | Yes |
| 50 | K stearate | lactitol | Me oleate | Yes |

Repeat of Example N.8 of GB-A-2,361,918

EXAMPLE 51

Example N.8 of GB-A-2,361,918 was repeated (342 grams sucrose, 2,160 grams methyl palmitate and 0.5 grams NaOH) using a domestic microwave and with the exception that the temperature was increased to 120° C. rather than 100° C. specified in Example N.8 (it is well known in the art that no reaction would be expected at 100° C. in the absence of a solvent). Samples were taken every hour for the specified time and for a further two hours, and analysed by T.L.C. in order to determine whether any sucrose ester could be detected. No sucrose ester formation could be detected.

EXAMPLE 52

Example 51 was repeated with the exception that the quantity of NaOH catalyst was increased 20 fold (10 grams) and samples were taken and analysed every hour for the specified time and for a further two hours. No sucrose ester formation could be detected.

EXAMPLE 53

Example 52 (increased quantity of catalyst) was repeated with the exception that the temperature was increased from 120° to 125-130° C. and samples were taken and analysed every hour for the specified time and for a further two hours. No sucrose ester formation could be detected.

EXAMPLE 54

Example 51 was repeated with the exception that methyl palmitate was replaced with methyl stearate. Samples were taken and analysed by T.L.C for the specified time and for a further two hours. No sucrose ester formation could be detected.

Figure 1:
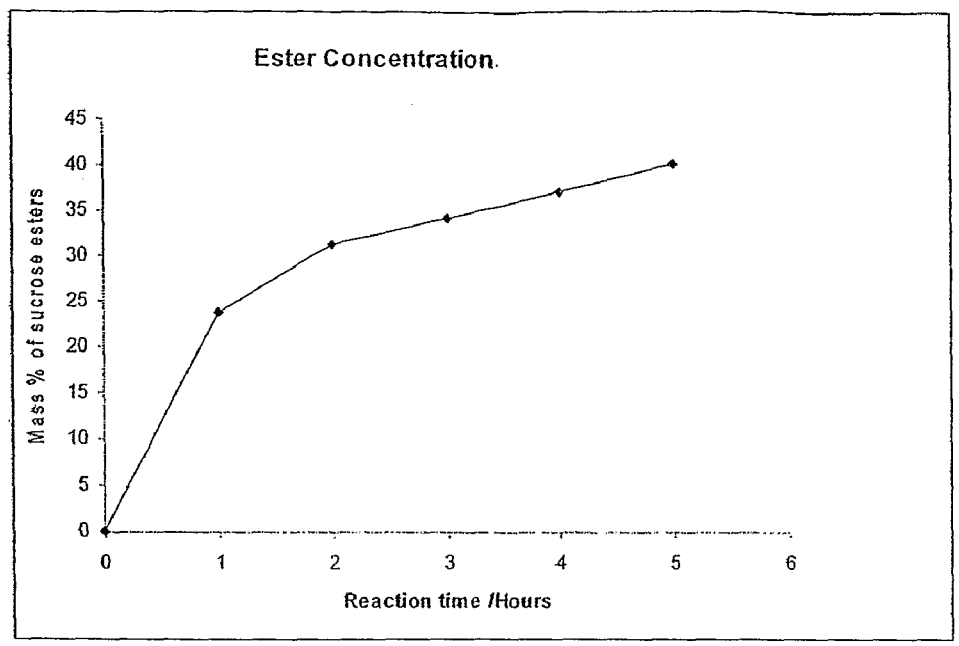
FIG. 1 is a graphical depiction of the results of Example 25.
Figure 2:
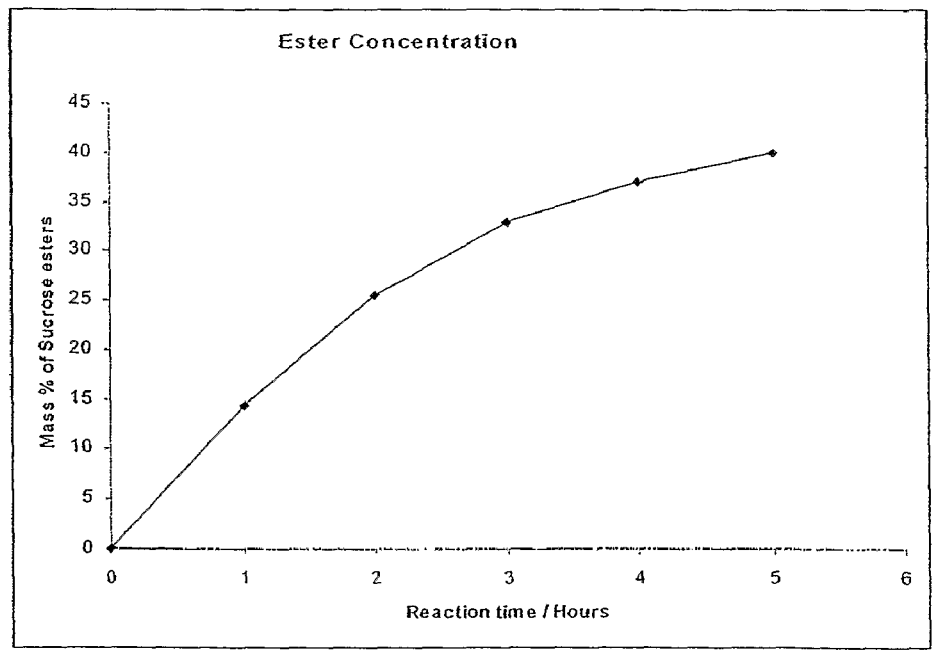
FIG. 2 is graphical depiction of the results of Example 26.

The invention claimed is:

1. A process for the production of mono- and di-esters of a non-reducing sugar, which comprises reacting the non-reducing sugar with a triglyceride of a fatty acid or a fatty acid ester of a monohydric alcohol in air at a pressure above 500 mbar, substantially in the absence of a solvent and under heterogeneous reaction conditions in which the non-reducing sugar and the fatty acid ester or triglyceride are present as separate phases, at a temperature in the range of from 110° C. to 140° C., wherein the reaction is conducted in the presence of a potassium soap and in the absence of an alkaline component.

2. A process as claimed in claim 1, wherein the sugar comprises a non-reducing disaccharide.

3. A process as claimed in claim 2, wherein the non-reducing disaccharide is sucrose or trehalose.

4. A process as claimed in claim 1, wherein the fatty acid alkyl ester has a straight-chain or branched, saturated, mono- or polyunsaturated fatty acid chain having a length in the range of from 6 to 22 carbon atoms.

5. A process as claimed in claim 4, wherein the fatty acid alkyl ester has a fatty acid chain in the range of from 12 to 18 carbon atoms.

6. A process as claimed in claim 1, wherein the fatty acid alkyl ester is an ester of a fatty acid with methyl, ethyl or propyl alcohol, or glycerol.

7. A process as claimed in claim 1, wherein the potassium soap has a chain length in the range of from 6 to 22 carbon atoms.

8. A process as claimed in claim 1, wherein the potassium soap has an unsaturated fatty acid chain.

9. A process as claimed in claim 8, wherein the potassium soap is potassium oleate.

10. A process as claimed in claim 1, wherein from 0.1 to 2 moles of sucrose are employed per mole of fatty acid alkyl ester.

11. A process as claimed in claim 1, wherein at least 0.4 moles of potassium soap is employed per mole of sugar.

12. A process as claimed in claim 11, wherein from 1 to 2 moles of potassium soap is employed per mole of sugar.

13. A process as claimed in claim 1, wherein up to 3 moles of potassium soap is employed per mole of sugar.

14. A process as claimed in claim 13, wherein up to 2.5 moles of potassium soap is employed per mole of sugar.

15. A process as claimed in claim 1, which is conducted at a temperature in the range of from 120-135° C.

16. A process as claimed in claim 1, which is conducted for a period of up to 15 hours.

17. A process as claimed in claim 12, which is conducted for a period of up to 5 hours.

18. A process as claimed in claim 1, wherein the reaction mix is continuously stirred in order to maintain a relatively even temperature.

19. A process as claimed in claim 1, which includes the step of isolating the ester of the non-reducing sugar from the reaction mix by means of solvent extraction.

20. A process as claimed in claim 19, wherein the solvent comprises an alkyl ester, a ketone, or an alcohol.

21. A process as claimed in claim 20, wherein the solvent comprises ethyl acetate, isopropanol, sec-butanol, or methyl ethyl ketone.

22. A process as claimed in claim 1, which is conducted in the absence of any conjugate base having a pKa value of more than 9.

23. A process as claimed in claim 1, which is conducted in the absence of any conjugate base having a pKa value of more than 6.5.

24. A process as claimed in claim 1, which is conducted in the absence of any conjugate acid having a pKa value of less than 4.

25. A process as claimed in claim 24, wherein the potassium soap has a chain length of at least 12 carbon atoms.

26. A process as claimed in claim 24, wherein the potassium soap has a chain length of not more than 18 carbon atoms.

* * * * *